United States Patent [19]

Holland

[11] Patent Number: 4,638,074

[45] Date of Patent: Jan. 20, 1987

[54] EXTRACTION OF TIN FROM ITS ORES

[75] Inventor: Frank S. Holland, Stockport, England

[73] Assignee: Manchem Limited, Manchester, England

[21] Appl. No.: 818,760

[22] Filed: Jan. 14, 1986

[30] Foreign Application Priority Data

Jan. 18, 1985 [GB] United Kingdom ............. 8501249

[51] Int. Cl.$^4$ .............................................. C07F 7/22
[52] U.S. Cl. ........................................ 556/98; 556/95
[58] Field of Search .................................. 556/95, 98

[56] References Cited

U.S. PATENT DOCUMENTS

| | | | |
|---|---|---|---|
| 2,625,559 | 1/1953 | Smith | 556/98 |
| 2,852,543 | 9/1958 | Blitzer et al. | 556/98 |
| 3,404,167 | 10/1968 | Gray et al. | 556/98 |
| 3,440,255 | 4/1969 | Matsuda et al. | 556/98 |
| 3,745,183 | 7/1973 | Katsumura et al. | 556/98 |
| 3,857,868 | 12/1974 | Witman et al. | 556/98 |
| 4,092,340 | 5/1978 | Jones | 556/97 |
| 4,179,458 | 12/1979 | Jones | 556/97 |
| 4,510,095 | 4/1985 | Holland et al. | 204/120 |

Primary Examiner—John Doll
Assistant Examiner—Wayne A. Langel
Attorney, Agent, or Firm—Cushman, Darby & Cushman

[57] ABSTRACT

A process for the direct recovery of tin, as an organo hydrocarbyl tin compound, from reduced but unrefined tin ores and ore slags is described, wherein the ore is reacted directly with a hydrocarbyl halide to form an organo hydrocarbyl tin compound which can then easily be removed and separated from the tin-depleted ore residue.

14 Claims, No Drawings

EXTRACTION OF TIN FROM ITS ORES

DESCRIPTION

This invention relates to the extraction of tin and tin values as organotin compounds directly from tin-bearing ores and wastes.

DISCUSSION OF PRIOR ART AND BACKGROUND OF THE INVENTION

Tin is found naturally in several minerals but only cassiterite ($SnO_2$) is of commercial importance. As the reduction of tin oxides is comparatively easy, tin is primarily extracted from the ore by pyrometallurgical reduction processes which involve smelting the ore, after concentrating the tin moety physically utilizing the high density of cassiterite.

Cassiterite ore occurs both as alluvial and lode deposits. The ore deposits, particularly the lode ores, are usually found associated with other materials which generally hinder tin refining to some extent. The presence of sulphur and iron is deterious during smelting while other elements such as As, Sb, Bi, Pb, Cu, and Ag necessitate further process steps during refining.

The reaction conditions for the reduction of tin dioxide are also appropriate for the reduction of the oxides of other metals which may be present. Iron is particularly troublesome owing to its mutual solubility with tin. In the usual temperature range at which tin refining is carried out, the solid in equilibrium with liquid tin is $FeSn_2$, the so-called "hard head", containing 19% iron by weight. Present methods of removing iron from tin depend on the crystallisation of $FeSn_2$ from liquid tin at low temperatures.

A number of processes have also been proposed from removing tin from slags and low grade material which depend on the formation of volatile inorganic tin compounds, notably the stannous oxide sulphide or chloride, to separate tin from the other elements, leading to the continuing use of the so-called fuming technique. A general review of methods is made in Extractive Metallurgy of Tin—P.A. Wright, Chapter 9 (1982). Also see Kirk-Othmer, Vol. 23, 3d Ed., pp. 21-24. In these methods tin ($SnCl_4$) removal is usually not affected by the presence of iron ($FeCl_3$).

Other methods for tin extraction include reduction hydrometallurgy which has been the subject of much investigation, previous work having been reviewed by Wright, supra.

Various proposals have been made to extract tin from its ores by reduction of cassiterite to tin metal and then extracting the tin with aqueous inorganic acids. Mantell, in Tin (second edition 1949) Chapter 7, describes a process wherein low temperature (ca. 750° C.) reduction is followed by countercurrent leaching and electrolytic deposition of tin giving a tin-depleted leach liquor for reuse. Mantell suggested that the combination of hydrogen reduction, leaching and electrolyte deposition of tin offered an economical method, with greater ease of operation than conventional smelting, and was capable of producing the highest grade of metal from the complex ores.

British patent specification GB No. 1278207 describes a similar process wherein finely divided tin ore is roasted, contacted with a gaseous reductant in a controlled moisture atmosphere and thereafter leached with dilute hydrochloric acid to remove tin metal and iron or iron compounds. The liquor extract is then contacted with a metal higher than tin in the electrochemical series to extract metallic tin by cementation.

However, it is clear that according to the methods described by Mantell and in the British specification that other metals present in the ore are also extracted by the acid leaching and there metals would build up in the leach liquor. It is therefore desirable to remove these other metals from the system. Consequently, GB No. 1278207 describes the use of a spray-roaster to recover hydrochloric acid and to remove the other metals from the system.

A further disadvantage of the acid/leach process is that after the roast/reduction stages, anions, such as fluoride—which is commonly associated with cassiterite deposits—will also be rendered soluble and extracted into the hydrochloric acid phase. As it is normally a necessary step in such processes to recover the hydrochloric acid for further use, the presence of other acids, particularly hydrofluoric acid, would be clearly undesirable as it would lead to the corrosive destruction of the spray roaster apparatus itself.

A somewhat different reduction process is described in GB No. 2060708. This patent describes a process in which aqueous or solvent-carried reducing agents are used to reduce the insoluble higher valency inorganic tin compounds in tin-bearing ores to form soluble lower valency stannous salts. The preferred reducing agents are divalent vanadium and divalent chromium ions. The solubilised tin is then electrolytically precipitated from the leach liquor and the reducing agent regenerated by further electrolysis.

Gaseous reduction of tin ores has been studied periodically over many years. The use of hydrogen or carbon monoxide gases has been most frequently proposed but other reducing gases such as commercial gases containing hydrogen and carbon monoxide mixtures and hydrocarbons have been used. Gas mixtures comprising $H_2/H_2O$ or $CO/CO_2$ have the particular advantage that minerals containing iron are reduced to $Fe_3O_4$ rather than elemental iron or FeO which are both leachable into acid solutions. Further, using such gas mixtures, tin/iron alloys such as "hard head" are prevented from forming.

Thus, the prior art dealing with the recovery of tin from its ores has relied on inorganic compound formation and/or heat or electrolytic means.

By contrast, the present invention has as its primary object an improved ore refining process which overcomes the foregoing disadvantages and which surprisingly provides for the direct production of valuable organotin compounds which may be used as such or which easily permit the recovery of substantially pure elemental tin from the ore without using electrolytic, fuming or like further heat treatments have which been commonly employed to date.

Even though the ore concentrate used in this invention as obtained from first an optional roasting or calcining followed by a reduction process dominantly still contains the various non-tin constituents and has only a relatively low percentage of tin content, we have now found it possible to directly react the unrefined ore with an organic halide, in the presence or absence of a catalyst, as a result of which the a relatively pure organo tin component may be directly extracted or obtained from the unrefined ore. The organo tin compound may be used as such is easily decomposed to provide highly purified elemental tin.

In its broadest aspect, therefore, the process of the present invention comprises optionally calcining ground concentrated tin ore to remove sulphides and any other interfering volatile constituents which may be present in the ore, then reducing the tin oxide content thereof, wholly or partially, to tin in a reducing atmosphere, preferably hydrogen, and contacting the resulting particulate solid composition with an organic halide, as defined herein, to form directly an organotin product which may then be readily extracted and purified. It is a particular advantage of the use of the process of this invention that few other elements will react with the organic halide reactant, as defined hereinafter, under the conditions of the process and accordingly it has now been discovered that tin can be directly extracted from the thus treated ore in the form of relatively pure organotin compounds, despite the presence of the other metal constituents in the ore.

For instance, typical ore concentrates such as are obtained from the cassiterite deposits in Cornwall, United Kingdom, may contain in addition to tin, zinc, aluminium, sulphur, iron and minor amounts of elements such as arsenic and bismuth derived from accompanying minerals. Much of the arsenic is removed during the initial calcining stage but any residual arsenic along with bismuth, may react with certain organic halides and could be collected in an organic phase along with the tin.

Other tin ore concentrates may also contain lead and/or antimony, which have not been removed during the calcining stage, but which may react with the organic halide and be extracted into the organic phase along with the tin. We have found, however, that these elements can easily be separated from the present organotin compound extracts by known methods. For example, organolead compounds can be cracked during distillation of the instant organotin compounds and thereby can be removed from the tin.

The organotin compounds extracted from the ores by this invention are valuable intermediate products for the production of other organotin compounds which have found many applications commercially such as synthetic polymer stabilisers, herbicides and fungicides. It is a feature of the invention that particularly desired organotin compounds can be directly manufactured by selection of particular organic halides and conditions under which the tin is extracted from the ores. For example, the tin may be extracted as dimethyltin dichloride when using methyl chloride as a reactant in the presence of a catalyst such as a trialkyl phosphine and/or a metal such as copper.

Even though the reaction of tin metal with certain organic compounds has long been known, and despite numerous prior efforts which have been devoted to improving the economics of the recovery of tin from low to medium, and even high grade ores, the present process which provides a direct extraction of tin from the unrefined ore has not been previously described or contemplated. That is, to the extent that the synthesis of the organotin compounds, as is involved in the present invention had been described (for many year) in the literature, prior workers have only used as the starting metal an already refined tin metal.

By contrast, the present invention bypasses the conventional refining stage and extracts the tin directly from the calcined, reduced, but unrefined ores to form the organotin compounds, even as a final commercial product, and which in any event permit a highly efficient extraction and recovery of tin values from the unrefined ores.

For instance, in the prior art it has long been known that pure elemental tin can be made to react with organic halides, usually in the presence of a catalyst, to form organotin halides or tetraorganotins. For example see the review articles by Murphy & Poller, "The Preparation of Organotin Compounds by the Direct Reactions", J. Organomet. Chem. Lib., (1979), 9, 189–222; and Kizlink, "Direct Synthesis of Organostannate Halides", Chem. Listy, (1984), 78, 134–145.

The direct reaction of tin metal with an organic halide in the presence of catalytic amounts of a quaternary ammonium and phosphonium compound or of a ternary sulphonium or iso-sulphonium compound to produce primarily mono- and diorganotin halides (possibly with triorganotin halides as a minor product) is disclosed in several earlier patent specifications for example, British specifications Nos. 1,115,646, 1,053,996 and 1,222,642, respectively also U.S. Pat. No.3,415,857, U.S. Pat. No. 3,745,183 and U.S Pat. No. 3,519,665.

GB No. 1,115,646 discloses reacting metallic tin (which may be used in powder, sheet or granule form, and may be part of an alloy especially with a co-catalyst) with an aliphatic halide in the presence of a catalyst, which is an 'onium compound (defined as a compound containing organic groups covalently bonded to a positively charged non-metallic atom from Group V or VI of the Periodic Table, and exemplified by tetraalkylammonium halides, tetraalkyl phosphonium halides and trialkylsulphonium halides) and in the presence of a pre-formed stannous halide or pre-formed organotin halide, and optionally in the presence of a small amount of a co-catalyst which is one of thirteen defined metals (said small amount being up to 0.1 mole per gram-atom of tin). The product of the reaction of GB No. 1,115,646 is a mixture of organotin halides in which the diorganotin dihalide predominates.

An earlier application by us, published as European Publication No. 0083981, now U.S. Pat. No. 4,510,095, describes a direct process for the production of organotin halides by the direct reaction of elemental tin metal with an organic halide in the presence of a compound of the formula $Cat^+X^-$, where $Cat^+$ is a cation and $X^-$ is a chloride, bromide or iodide ion and wherein elemental tin is reacted with the organic halide in the presence of the compound $Cat^+X^-$, which is in the liquid state, while maintaining the concentration of the organic halide relative to the compound $Cat^+X^-$ throughout the reaction period at a level such that there is produced an organotin halide product in which the predominant molecular species is a triorganotin halide in association with a water insoluble halogenotin complex containing tin and $Cat^+X^-$ in combined form.

U.S. Pat. No. 3,651,108 has also described the preparation of tetraorganotin compounds by reaction of organic halides in the presence of an 'onium' compound, or Lewis base, with tin metal and an alkali or alkaline earth metal, in particular magnesium. Similarly U.S. Pat. Nos. 4,179,458 and 4,092,340 describe processes for preparing tetraorganotin compounds which comprise reacting an organic halide of formula RX with a heated suspension of metallic material which is zinc and tin (in the atomic proportions of at least 0.5 to 1) in a liquid comprising at least one 'onium salt,' which salt is an organic quaternary ammonium or phosphonium or tertiary sulphonium salt, to produce the tetraorganotin compound. In U.S Pat. No. 4,179,458 this agent is a liquid, in U.S. Pat. No. 4,092,340, it is a gas. From the examples given in these two cases, the processes appear to be

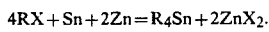

$$4RX + Sn + 2Zn = R_4Sn + 2ZnX_2.$$

The liquid 'onium' compound functions as a solvent.

Metals have also been proposed as catalysts in the direct synthesis of organotin halides from the refined metal. Smith and Rochow in J. Amer. Chem. Soc. 75, 4103 (1953) investigated the effects of metals and reported catalytic activity with copper, silver and gold with copper being the most promising catalyst.

Kizlink, in his review article, supra, mentions several prior proposals on the direct synthesis of organotin compounds with methyl chloride which is usually carried out by introducing methyl chloride into molten tin metal with additives which may be Ag, Cu, Zn, Mg or Al. These latter metals are capable of forming unstable metal organic compound which may aid the reaction in this way.

Overall, however, and as can be seen from the prior art, the direct synthesis of organotin halides or tetraorganotins as reported in the literature has required and has only been described as using expensive, already refined substantially pure tin metal, mainly in powder form, or its alloys.

That is, in all of the cases described above the tin used had already been extracted from the ore by conventional processes and was further refined before use in the organotin process.

Accordingly, in one aspect of the present invention, an organotin product containing predominately diorganotin dihalide is produced directly by reacting a comminuted, optionally calcined, reduced but unrefined ore concentrate with an organic halide and catalyst. Conditions for this reaction may be as described in GB No. 1,115,646.

According to another aspect of the invention, a product containing predominately triorganotin halide can be produced by extracting the tin from a calcined, reduced but unrefined ore concentrate. Conditions for this reaction may be as described in U.S. Pat. No. 4,510,095.

In a further aspect of this invention, zinc may be added to the unrefined ore concentrate and the same then reacted according to the conditions described in GB No. 1,548,365 to directly obtain a product containing predominately tetraorganotin.

The disclosures of GB No. 1,115,646; U.S. Pat. No. 4,510,095 and GB No. 1,548,365 are incorporated herein by reference.

According to the present invention, tin is directly extracted from its unrefined ores as a compound of the formula $R_aSnX_{(4-a)}$ wherein each R represents an organic radical covalently bonded to the tin, especially a hydrocarbyl group, preferably containing up to 20 carbon atoms and selected from the class of alkyl (including cycloalkyl) e.g. butyl and cyclohexyl, alkenyl e.g. but-3-enyl, aralkyl e.g. benzyl, alkaryl e.g. 3-methylphenyl, aryl e.g. phenyl and aralkenyl e.g. 4-phenyl-but-2-enyl, X is a halogen atom selected from chlorine, bromine and iodine and a is a number from 1 to 4.

The products separated from the (now) tin-depleted ore residues are usually a mixture of organotin halides (except when zinc is added to the ore concentrate which yields a tetraorganotin) and residual reagents and/or catalysts. The tin compounds thus formed are generally liquid at normal temperatures which facilitates the separation from the ore residue.

These products can be treated in several ways already known to those skilled in the art to purify them or to recover the highly purified tin metal therefrom. Generally it is preferred that the organotin halides are purified by either solvent extraction or by distillation, with the reagents and/or catalysts so used then recovered for further re-cycled use.

The distilled organotin halides can themselves be further purified, for example, by fractional distillation, to separate the diorganotins (which can be used directly as stabilisers) or the triorganotins (which are useful as biocides or as starting materials for the production of other triorganotin compounds). It is also useful to use diorganotin and triorganotin halide mixtures now obtained directly from the unrefined ore concentrate as the starting material for the process of U.S. Pat. No. 4,510,095.

Alternatively, the organotin halide mixtures may also be thermally decomposed to give pure elemental tin.

The tin concentrates used in the process of the invention may be low grade primary extracts containing as little as 5% tin such as from cassiterite up to high grade extracts containing about 70% $SnO_2$. The invention can also be applied even to low grade slags, obtained in ore processing, which typically contain only about 2 to 3% tin. There are substantial quantities of such slags left as by-products from conventional refining techniques from which the residual (now wasted) tin values can now be recovered.

The organic halides used in this invention are of the formula RX where both R and X are as defined above. Depending on the organotin product desired, the organic halide may be used in amounts of from less than 1 mole per gram-atom of tin present in the concentrate during the reaction to a considerable excess of up to about 5 times of the theoretical quantity for organotin formation.

The preferred organic catalyst for the tin extraction is an 'onium' compound as defined in GB No. 1,156,646 (U.S. Pat. No. 3,415,857) and is normally present in an amount of from 0.1 to 0.6, preferably 0.2 to 0.5 moles per gram-atom of tin in the tin ore concentrate.

Alternatively, the 'onium' compounds may be present in only reagent amounts as is described in U.S. Pat. No. 4,510,095 where about 4 moles of RX are used per mole of reagent and suitably there is at least one mole of reagent per 5 moles of RX.

According to one embodiment of the process of the present invention, finely ground tin ore, wherein the tin in the tin bearing materials has been reduced to elemental tin by gaseous reduction, is heated together with an organic halide and an 'onium' compound at a temperature preferably between 100°–200° C. under reflux conditions for such a time until substantially all the tin content in the ore concentrate has dissolved. The resulting mixture of soluble organotin compounds is then separated and washed from the ore residue by solvent extraction using an organic solvent. A suitable solvent may be the organic halide reagent. The combined liquid phases are then distilled to remove the solvent (for reuse) and a residue of organotin compounds remains. This residue may now be further purified, (e.g. by distillation) thermally decomposed or used as a starting material for the production of other organotin compounds.

In an alternative process according to the invention, ground, calcined tin ore concentrates, which have been reduced by gaseous reduction, are mixed with a metallic catalyst and heated at a temperature in the range of 300°-400° C. while passing an organic halide in the gaseous state over the same. The resulting vapors containing the organotin product are then condensed and purified by any of the methods already known to those skilled in the art for those products.

The initial calcining of the ore concentrate may be omitted whenever the ore impurities are in low concentrations and/or do not present a problem in obtaining the desired organotin compound.

By whatever method the process of this invention is effected, this invention has further discovered that the presence of other elements naturally present in the ore concentrates such as copper, zinc, etc. turns out to be in fact useful in that it is now found that such metals are in a form in the ore concentrate such that they can act as in situ catalysts which thereby may make the addition of any further catalyst unnecessary.

A preferred gaseous reduction mixture for use on the calcined ore is $H_2/H_2O$ which ensures that any combined iron values present in the ore concentrate are not reduced to iron metal which could alloy with the tin or react with the organic halide when it is passed over the ore. In addition, and if desired and appropriate with a given ore composition following reduction a re-oxidation stage may be employed to convert the iron to iron oxide. This has the advantage that iron oxide does not react with the organohalides and consequently on that basis a greater efficiency in forming organotin halides can be realized.

5.7% total tin, was heated with butyl bromide (234 g) containing tetrabutylammonium bromide (58 g) at reflux temperature for 70 hours. The liquid phase was separated and the solid residue washed with butyl bromide until the washings were colourless. The combined liquid phases were distilled on a rotary evaporator leaving a residue (88 g) which analyzed at 7.4% tin and 37.33% bromine.

This indicates that approximately 34% of the tin in the ore had been extracted.

EXAMPLES 2-4

Crushed samples of Cornish cassiterite concentrates ($-1400$ $\mu$m) of various grades were roasted and then reduced in an electric furnace by heating to 730° C. whilst passing air through the furnace, then sequentially purging with nitrogen, passing hydrogen and finally flushing out with nitrogen as shown in Table 1. All the products were cooled to room temperature under nitrogen and were stored under nitrogen in a desiccator.

TABLE 1

ROASTING AND REDUCTION OF CASSITERITE ORE AT 730° C.

EXPERIMENTAL CONDITIONS

| | ROASTING | | | | | REDUCTION | | | |
|---|---|---|---|---|---|---|---|---|---|
| MATERIALS USED | WEIGHT REDUCED (g) | AIR FLOW (mls min$^{-1}$) | TIME AT TEMP (mins) | NITROGEN FLUSH | | $H_2$ FLOW (mls min$^{-1}$) | TIME AT TEMP (mins) | NITROGEN FLUSH | |
| | | | | $N_2$ FLOW (mls min$^{-1}$) | TIME (mins) | | | $N_2$ FLOW (mls min$^{-1}$) | TIME (mins) |
| HIGH GRADE CONCENTRATE (40.41% Sn) | 100 | 600 | 60 | 600 | 10 | 600 | 348 | 600 | 10 |
| | 50 | 600 | 30 | 600 | 10 | 600 | 224 | 600 | 10 |
| LOW GRADE CONCENTRATE (10.35% Sn) | 100 | 600 | 73 | 600 | 10 | 200 | 324 | 600 | 10 |
| | 50 | 600 | 37 | 600 | 10 | 200 | 162 | 600 | 10 |
| ROUGH CONCENTRATE (4.33% Sn) | 100 | 600 | 62 | 600 | 10 | 200 | 132 | 600 | 10 |
| | 50 | 600 | 31 | 600 | 10 | 200 | 66 | 600 | 10 |

Analysis of the reduced concentrates indicated complete reduction of the tin compounds present in amounts of from about 13 to 53 wt %.

Samples of the resulting reduced concentrates were then mixed with copper powder catalyst, heated to 315° C. in an electric furnace whilst passing over gaseous methyl chloride, and held at this temperature for the periods of time indicated in Table 2. Analysis of the residue indicated an extraction of 80 to 95% of the tin.

The gaseous products were then scrubbed using dichloromethane and analyzed for chlorine content,

TABLE 2

REACTION WITH ORGANIC HALIDE

| | Starting Materials | | | | Methyl | Residue | | Product Analysis* | |
|---|---|---|---|---|---|---|---|---|---|
| Example | Reduced Cassiterite g | Tin Content g | Cu Catalyst g | Time at 315° C. hours | Chloride flow rate mls/min | Weight g | Tin Content g | Tin Removed % | Cl % | Melting Point °C. |
| 2 | 42.40 | 5.475 | 1 | 5.2 | 60 | 44.06 | 1.03 | 81 | 33.1 | 104 |
| 3 | 42.03 | 5.475 | 1 | 5.2 | 120 | 43.65 | 1.11 | 80 | 32.0 | 104 |
| 4 | 11.82 | 6.25 | 1 | 5.0 | 120 | 8.63 | 0.34 | 95 | 32.0 | 105 |

*Theoretical chlorine content of dimethyltin dichloride is 32.3% and melting point is 107-108° C.

EXAMPLES

The invention is further illustrated by reference to the following examples:

EXAMPLE 1

Concentrated tin ore (334 g) which had been ground, calcined and reduced with hydrogen, and assayed at which with melting point indicated a recovery of dimethyl tin dichloride.

EXAMPLES 5-6

Cornish cassiterite concentrates ($-1400$ $\mu$m) were roasted and then reduced in an electric furnace as described in Examples 2-4.

Samples of the roast/reduced materials of varying tin concentration were then refluxed at 100°–105° C. with butyl bromide and with tetrabutylammonium bromide as catalyst as shown in Table 3.

Product separation was effected by filtration, washing with butyl bromide and finally washing with acetone. The solvent was removed by distillation and the residual product distilled under vacuum and collected in cold traps.

On analysis, the product was shown to be a mixture of mono-, di- and tributyltin bromides and the level of tin extraction was from 34 to over 60%.

which increased to 75% when extraction time was extended to 26.5 hours.

TABLE 4

EXTRACTION OF TIN USING METHYL CHLORIDE IN A STIRRED REACTOR

| | Starting materials | | | Time at 310° C. | Methyl chloride flow rate | Residue | | | Wt. tin in organotin product g |
|---|---|---|---|---|---|---|---|---|---|
| Example | Reduced Cassiterite g | Tin content g | Cu Catalyst g | hours | mls/min | Weight g | Tin content g | Tin removed % | |
| 7 | 168.5 | 20.6 | — | 28.75 | 120 | 190.2 | 2.96 | 85.6 | 9.1 |
| 8 | 168.5 | 21.25 | 4 | 10.92 | 120 | 190.5 | 9.79 | 54.0 | 12.73 |
| 9 | 168.5 | 20.82 | 4 | 26.5 | 120 | 191.3 | 4.05 | 80.5 | 15.55 |

TABLE 3

EXTRACTION OF TIN USING BUTYL BROMIDE

| | Starting materials | | | Time at 100–105° C. | Butyl bromide addition g | Vacuum distillation product | | | |
|---|---|---|---|---|---|---|---|---|---|
| Example | Reduced Cassiterite g | Tin content g | Catalyst g | hours | | g | % Br | % Tin extracted | |
| 5 | 210.94 | 9.81 | 2.53 | 112.3 | 435 | 37.36 | 55.17 | 60.5 | |
| 6 | 18.95 | 8.96 | 2.53 | 112.3 | 315 | 11.49 | 42.7 | 34.1 | |

EXAMPLES 7–9

Cornish cassiterite ore concentrates were roasted and then reduced in an electric furnace as described in Examples 2–4.

Samples of the roasted/reduced materials (optionally mixed with copper catalyst Examples 8, 9) were heated with stirring in a 2500 ml round bottom glass reactor into which methyl chloride was blown.

The gaseous products were scrubbed using dichloromethane and analyzed. A summary of the experimental conditions and analysis of the products which comprised mixtures of mono-, di- and trimethyltin chlorides, is given in Table 4.

In Example 7, a recovery of 44% was achieved even without a catalyst. In Example 8 the recovery was 60%,

EXAMPLES 10–16

Cornish cassiterite ore concentrates were roasted and then reduced in an electric furnace by heating to 730° C. whilst passing air through the furnace then sequentially purging with nitrogen, passing hydrogen or hydrogen saturated with water, flushing out with nitrogen and finally reoxidizing (as required) as shown in Table 5. Examples 10–14 illustrate the effects of changing amounts of water used in the reduction stage. In Examples 15 and 16 no water is used, and in Example 16 a post-reduction re-oxidation is used which selectively reoxidizes the iron (but not the tin).

TABLE 5

ROASTING AND REDUCTION OF CASSITERITE ORE AT 730° C. WITH DIFFERING REACTION CONDITIONS

| | Experimental conditions | | | | | | | | | | | | |
|---|---|---|---|---|---|---|---|---|---|---|---|---|---|
| | Roasting | | | Nitrogen flush | | Reduction | | | Nitrogen flush | | Reoxidation | | |
| Material for Example | Weight g | Air flow mls/min | Time mins | $N_2$ flow mls/min | Time mins | $H_2$ flow mls/min | Time mins | $H_2O$ at °C. | $N_2$ flow mls/min | Time mins | Air flow mls/min | Temp °C. | Time mins |
| 10 | 100* | 600 | 74 | 600 | 10 | 400 | 162 | Not used | 600 | 10 | Not done | — | — |
| 11 | 100* | 600 | 74 | 600 | 10 | 400 | 162 | 34 | 600 | 10 | " | — | — |
| 12 | 100* | 600 | 74 | 600 | 10 | 400 | 162 | 56 | 600 | 10 | " | — | — |
| 13 | 100* | 600 | 74 | 600 | 10 | 400 | 162 | 67 | 600 | 10 | " | — | — |
| 14 | 100* | 600 | 74 | 600 | 10 | 400 | 162 | 79 | 600 | 10 | " | — | — |
| 15 | 100* | 600 | 74 | 600 | 10 | 400 | 196 | Not used | 600 | 10 | " | — | — |
| 16 | 100* | 600 | 74 | 600 | 10 | 400 | 196 | Not used | 600 | 10 | 600 | 140 | 30 |

*Duplicated

Samples of roasted/reduced materials of varying tin content were next mixed with copper powder catalyst and heated with stirring in a 2500 ml round bottom glass reactor into which methyl chloride was blown.

The gaseous products were scrubbed and analyzed for tin content. The experimental conditions and analysis of the resulting products, which comprised mixtures of mono-, di- and trimethyl tin chlorides, are given in Table 6.

The results of Examples 10–14 suggest that the amount of water used in the reduction stage should be optimized for maximum organotin extraction.

TABLE 6
EXTRACTION OF TIN USING METHYL CHLORIDE FROM CASSITERITE REDUCED BY DIFFERENT MEANS

| Example | Starting materials | | | Time at 310° C. hours | Methyl chloride flow rate mls/min | Residue | | Tin removed % | Wt. tin in organotin product g |
| --- | --- | --- | --- | --- | --- | --- | --- | --- | --- |
| | Reduced Cassiterite g | Tin content g | Cu Catalyst g | | | Weight g | Tin content g | | |
| 10 | 168.5 | 21.53 | 4 | 4 | 120 | 174.89 | 10.02 | 53.5 | 8.96 |
| 11 | 158.0 | 20.02 | 3.75 | 4 | 120 | 162.75 | 7.88 | 60.6 | 9.61 |
| 12 | 158.0 | 19.94 | 3.75 | 4 | 120 | 158.40 | 6.67 | 66.6 | 11.49 |
| 13 | 158.0 | 20.29 | 3.75 | 4 | 120 | 165.1 | 11.74 | 42.1 | 8.26 |
| 14 | 158.0 | 20.94 | 3.75 | 4 | 120 | 156.43 | 12.39 | 40.8 | 7.75 |
| 15 | 134.1 | 20.28 | 3.75 | 4 | 120 | 146.66 | 7.71 | 62.0 | 9.68 |
| 16 | 133.8 | 20.32 | 3.75 | 4 | 120 | 131.85 | 6.82 | 66.4 | 6.47 |

Other modifications of the specific methods shown in the above Examples will be apparent to those skilled in the art within the general principles and mode of operation of this invention as described above.

What is claimed is:

1. A process for the direct recovery of tin from reduced but unrefined tin ores and ore slags of a tin content of at most about 70 wt % which consists essentially in
   forming a comminuted, reduced but unrefined tin ore of fine particles;
   treating said unrefined tin ore with a hydrocarbyl halide to form an organo hydrocarbyl tin compound; and
   separating said organo hydrocarbyl tin compound from the tin-depleted solid ore residues.

2. The process of claim 1 wherein said ore is first calcined prior to reduction thereof.

3. The process of claim 1 wherein said hydrocarbyl halide is of the formula RX wherein R represents a hydrocarbyl radical containing up to 20 carbon atoms and X is chlorine, bromine or iodine.

4. The process of claim 3 wherein said hydrocarbyl radical is selected from the class of alkyl, alkenyl, aralkyl, and aralkenyl.

5. The process of claim 2 wherein said hydrocarbyl halide is of the formula RX wherein R represents a hydrocarbyl radical containing up to 20 carbon atoms and X is chlorine, bromine or iodine.

6. The process of claim 5 wherein said hydrocarbyl radical is selected from the class of alkyl, alkenyl, aralkyl, and aralkenyl.

7. The process of claim 1 wherein an 'onium' compound is present in an amount of from 0.1 to 0.6 moles per gram atom of tin in the unrefined tin ore or tin slag.

8. The process of claim 7 wherein said 'onium' compound is present in an amount from 0.2 to 0.5 moles per gram atom of tin in the reduced, unrefined tin ore or tin slag.

9. The process of claim 7 wherein the reduced, unrefined tin ore or tin slag is heated with the hydrocarbyl halide and 'onium' compound at a temperature between 100° and 200° C. under reflux.

10. The process of claim 9 wherein the organo hydrocarbyl tin compounds formed are separated from the tin-depleted ore residues by solvent extraction.

11. The process of claim 1 wherein the reduced, unrefined tin ore is heated at a temperature of from 300° to 400° C. while passing thereover the hydrocarbyl halide compound in the gaseous state, and thereafter condensing the organo hydrocarbyl tin compounds from the resulting vapors.

12. The process of claim 11 wherein a metallic catalyst is present.

13. The process of claim 12 wherein the metal content of the unrefined tin ore is utilized as in situ metallic catalyst.

14. The process of claim 1 wherein prior to heating said unrefined tin ore with a hydrocarbyl halide, said ore is reoxidized to convert elemental iron therein to iron oxides.

* * * * *